United States Patent [19]
Park et al.

[11] Patent Number: 5,800,467
[45] Date of Patent: Sep. 1, 1998

[54] CARDIO-SYNCHRONOUS IMPEDANCE MEASUREMENT SYSTEM FOR AN IMPLANTABLE STIMULATION DEVICE

[75] Inventors: Euljoon Park, Stevenson Ranch; Kerry Bradley, Pasadena; Gene A. Bornzin, Simi Valley; Joseph J. Florio, Sunland, all of Calif.

[73] Assignee: Pacesetter, Inc., Sylmar, Calif.

[21] Appl. No.: 766,641

[22] Filed: Dec. 13, 1996

Related U.S. Application Data

[60] Provisional application No. 60/008,731 Dec. 15, 1995.
[51] Int. Cl.$^6$ .................................................. A61N 1/368
[52] U.S. Cl. ............................................................. 607/17
[58] Field of Search .................................... 607/17, 24, 23

[56] References Cited

U.S. PATENT DOCUMENTS

| | | |
|---|---|---|
| 4,733,667 | 3/1988 | Olive et al. .................. 607/24 |
| 5,224,475 | 7/1993 | Berg et al. . |
| 5,361,776 | 11/1994 | Samuelson et al. . |
| 5,385,576 | 1/1995 | Noren et al. . |
| 5,447,521 | 9/1995 | Anderson et al. . |
| 5,507,780 | 4/1996 | Finch . |
| 5,553,611 | 9/1996 | Budd et al. . |
| 5,562,712 | 10/1996 | Steinhaus et al. . |

FOREIGN PATENT DOCUMENTS

| | | |
|---|---|---|
| 0574608A1 | 12/1993 | European Pat. Off. . |
| 0625690 | 9/1978 | U.S.S.R. . |

OTHER PUBLICATIONS

Schaldach, M., "Intracardiac Impedance to Determine Sympathetic Activity in Rate Responsive Pacing", *PACE*, vol. 15, Part II, pp. 1778–1786, (Nov. 1992).

*Primary Examiner*—Scott M. Getzow

[57] ABSTRACT

In a pacing system, the pacing controller induces the leads to deliver an impedance measurement pulse to the right ventricle of the heart at at least a 15 ms interval during a window of time following detection of the R-wave or the delivery of a pacing pulse. The window of time corresponds to a period of ventricular ejection. The two or three measured impedance values are then used to determine an impedance slope that has a strong biological correlation to the contractility of the heart. The impedance slope is then used by the controller of the pacing system to adjust the delivery of pacing pulses for purposes such as maximizing contractility for a given AV delay, PV delay and pacing rate of pacing pulses.

34 Claims, 4 Drawing Sheets

CARDIO-SYNCHRONOUS IMPEDANCE MEASUREMENT SYSTEM FOR AN IMPLANTABLE STIMULATION DEVICE

This application claims the benefit of U.S. Provisional application Ser. No. 60/008,731 Dec. 15, 1995.

FIELD OF THE INVENTION

The present invention relates to implantable electrical devices and, more particularly, concerns a system for use with the heart for optimizing heart performance by measuring the impedance within the heart synchronously with the detection of a ventricular contraction.

BACKGROUND OF THE INVENTION

Implantable electrical devices are increasingly used in patients for therapy for various physical ailments. In particular, one very common type of implantable electrical device is the pacemaker. A pacemaker is an implantable electrical device that has leads that are positioned within the heart so that therapeutic shocks can be provided to the heart to regulate heart function. Since their initial use, pacemakers have become increasingly sophisticated to the point where pacemakers are capable of sensing the function of the heart and providing therapeutic shocks that are both configured and timed to optimize the pumping function of the heart.

For example, it is understood that by varying the pacing rate, i.e., the frequency at which the heart beats, the efficiency of the heart in pumping blood can be varied. Similarly, the timing of a therapeutic shock applied to the heart from a pacemaker can also vary the AV delay and/or the PV delay, i.e., the delay between the contraction of the atrium and the ventricle, to also improve the efficiency of the pumping function of the heart.

While pacemakers have become sufficiently sophisticated to be able to time the therapeutic shocks being applied to the heart to vary these two parameters, the ability to do so requires that there be various sensors positioned within the heart that provide the controller of the pacemaker information indicative of the function of the heart. For example, the pacemaker lead that is positioned within the ventricle provides an electrocardiogram signal to the pacemaker controller that is indicative of the electrical stimulation and contraction of the heart. This signal can be used by the controller to determine when pacing therapeutic shocks are needed.

It is also known that the measured impedance of the heart within the ventricle also provides an indication as to the contractility of the heart. Contractility is the degree of contraction that the heart is experiencing during its pumping function. It is well understood that the greater contractility of the heart, the greater volume of blood being pumped by the heart for any given heart rate. The impedance measured within the ventricle during contraction increases contemporaneously with the increase in pressure within the contracting ventricle. Consequently, it is understood that by measuring the impedance within the ventricle, an indication as to the contractility can be provided to the controller.

This information can be used by the controller for a number of purposes such as adjusting the AV delay and pacing rate to optimize the heart's pumping function. However, it will be appreciated that to measure impedance, within the right ventricle of the heart, requires that electrical energy be transmitted into the ventricle of the heart so that the impedance can then be calculated. Typically, current is applied between the tip or the ring and the pacemaker case, so that the impedance can be measured therebetween. For example, U.S. Pat. No. 5,003,976, U.S. Pat. No. 4,919,136 and U.S. Pat. No. 4,901,725 disclose measuring the impedance signal between the ring/tip electrode and the pacemaker case with an alternating current source applied therebetween. In U.S. Pat. No. 4,901,725, the impedance signal is measured between the tip electrode and the pacemaker case with the current source being applied between a ring electrode and the pacemaker case.

Regardless of the method used to measure the impedance, the impedance measurement compromises the longevity of the battery that is powering the pacemaker device. In particular, it is desirable to be able to measure the impedance fairly often so that the impedance measurement can be used for optimizing the performance of the pacemaker and the function of the heart. However, each time the impedance signal is measured, current is drained out of the battery, simply for the purpose of measuring the impedance. This drain on the battery, of course, reduces the longevity of the battery and, therefore, reduces the longevity of the device itself.

Most prior art, such as the devices disclosed in U.S. Pat. Nos. 5,235,976, 5,190,035, 5,058,583 and 4,674,518 use a relatively fast measuring frequency, e.g., 1–12 kHz, to recover the entire impedance waveform and to extract certain impedance parameters. These parameters include the active time (U.S. Pat. No. 5,235,976), the ejection fraction (U.S. Pat. No. 5,154,171), and the time interval between a paced beat or spontaneous R-wave to zero crossing of the impedance signal in the positive direction (U.S. Pat. No. 5,773,401). While each of these impedance parameters provides information to the processor which is helpful for optimizing the performance of the pacemaker and of the heart, each of these devices still suffers from an unreasonable drain on the battery of the pacemaker.

Another approach has been suggested by M. Shaldach in an article entitled "Intracardiac Impedance to Determine Sympathetic Activity in Rate-Responsive Pacing", published in *PACE Magazine*, November 1992, Volume 15, No. 11, Part 2, page 1178, wherein the local slope changes of an entire impedance signal within a predetermined window were measured. It was suggested in this article that this information could be used as an indication of the sympathetic activity of the autonomous nervous system. While this approach may provide some indication as to the electrical functioning of the heart, there is still the difficulty of an inordinate amount of battery power being consumed for the measurement.

Hence, from the foregoing, it should be apparent that there is a need for a way of obtaining an electrical signal that is indicative of the contractility of the heart without significantly draining the battery of a pacemaker. To this end, there is a need for a system that is capable of obtaining an impedance related parameter during the contraction of the heart while using a reduced amount of battery power to obtain the signal. Preferably, this impedance parameter should still have a high correlation to the contractility of the heart and thereby provide a good indication as to the contractility of the heart.

SUMMARY OF THE INVENTION

The aforementioned needs are satisfied by the system of the present invention which is comprised of an implantable electrical device having at least one lead positioned within a contracting chamber of the heart. The implantable electrical device should also receive signals from a sensor indicative of the occurrence of a spontaneous R-wave of the heart or a paced beat of the heart. Subsequently, the system then applies current to the lead so as to obtain an impedance signal at at least two points during a window of time following the R-wave or paced beat during which contraction of the chamber of the heart occurs. The system then uses the at least two measured impedances to calculate the slope of the change in impedance (dz/dt) of the heart during this interval.

The Applicant has determined that the slope of change of impedance measured during a time interval around late rapid ventricular ejection and early reduced ejection is strongly correlated to the maximum slope of the ventricular pressure of the ventricular ejection. In the preferred embodiment, only a single slope measurement is made (e.g., using two or three impedance measurements) during this window wherein each impedance measurement is taken, for example, at a 64 Hz sampling rate, to achieve two measurements approximately 15.6 milliseconds apart. The Applicant has determined that the biological correlation between the impedance slope and the maximum slope of the ventricular pressure under sinus conditions and also under pacing conditions is very high. This signal can therefore be used as an indication as to the contractility of the heart. This indication can then be used by the system to alter the performance of the pacemaker to optimize the function of the heart. In particular, the parameter can be used for purposes such as rate adaptive pacing, altering AV delay, or altering the selected pacing rate of the heart so that the volume of blood pumped by the heart is maximized for each heartbeat.

It will be appreciated that taking the measurements at two or three discrete intervals during this window wherein a high biological correlation between the measurements and the contractility of the heart occurs, results in a parameter that can be used for controlling the function of a pacemaker while minimizing the drain on the battery powering the pacemaker. In particular, the impedance parameter can be obtained by injecting current down the lead at at least two discrete time periods as opposed to measuring the impedance over the entire waveform. These and other objects and advantages of the present invention will become more fully apparent from the following description taken in conjunction with the accompanying drawings.

DETAILED DESCRIPTION OF THE PREFERRED EMBODIMENT

Figure 1:
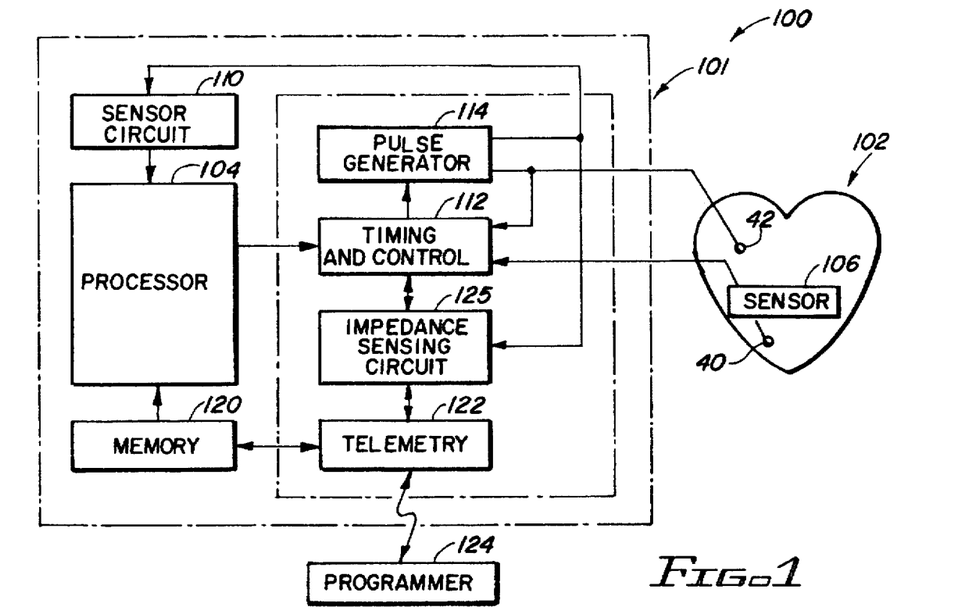
FIG. 1 is a block diagram illustrating the functional components of a pacemaker system of the preferred embodiment.

Reference will now be made to the drawings wherein like numerals refer to like parts throughout. Reference will now be made to FIG. 1 which is a schematic illustration of a pacing system 100 that is used to regulate the function of a heart 102. The pacing system 100 includes a controller 101 that comprises a processor 104 that receives signals from a sensor 106 via a sensor circuit 110 which are indicative of the function of the heart 102. As is generally understood in this art, the sensor 106 is typically comprised of a pacing lead 40 that is implanted into an apex 140 of a right ventricle 142 of the heart. In response to the signals received from the sensor 106, the processor 104 can trigger a timing and control circuit 112 and a pulse generator circuit 114 to apply therapeutic shocks, i.e., electrical impulses, to the heart 102 via one or more leads positioned within the heart 102 for pacing purposes.

Further, the pacing system 100 is also configured so as to have a telemetry circuit 122 wherein information stored in the memory 120 can be downloaded to an external programmer 124 and instructions from the external programmer 124 can be provided to the processor 104 in a manner well known in the art. The operation of the controller 101 and the pacing system 100 in this respect is typical of the operation of known prior art pacing systems.

The pacing system 100 in this embodiment also includes an impedance sensing circuit 125 that makes periodic determinations of the impedance within the right ventricle of the heart in response to signals from the processor 104. Briefly, the processor 104 periodically triggers the pulse generator 114 to transmit a current pulse into the heart via one of the electrodes positioned within the heart. (While the pulse generator 114 is generally a constant voltage pulse generator for purposes of generating stimulation pulses, for convenience, the present invention describes the pulse generator 114 to include circuitry for constant current measurement pulses. Alternatively, the constant current measurement pulses could have been shown as a separate block.) The voltage is then measured by the impedance sensing circuit 125 and the instantaneous impedance is then calculated. These calculated values can then be used to obtain an impedance slope dz/dt in the manner that will be described in greater detail hereinbelow.

Figure 2:
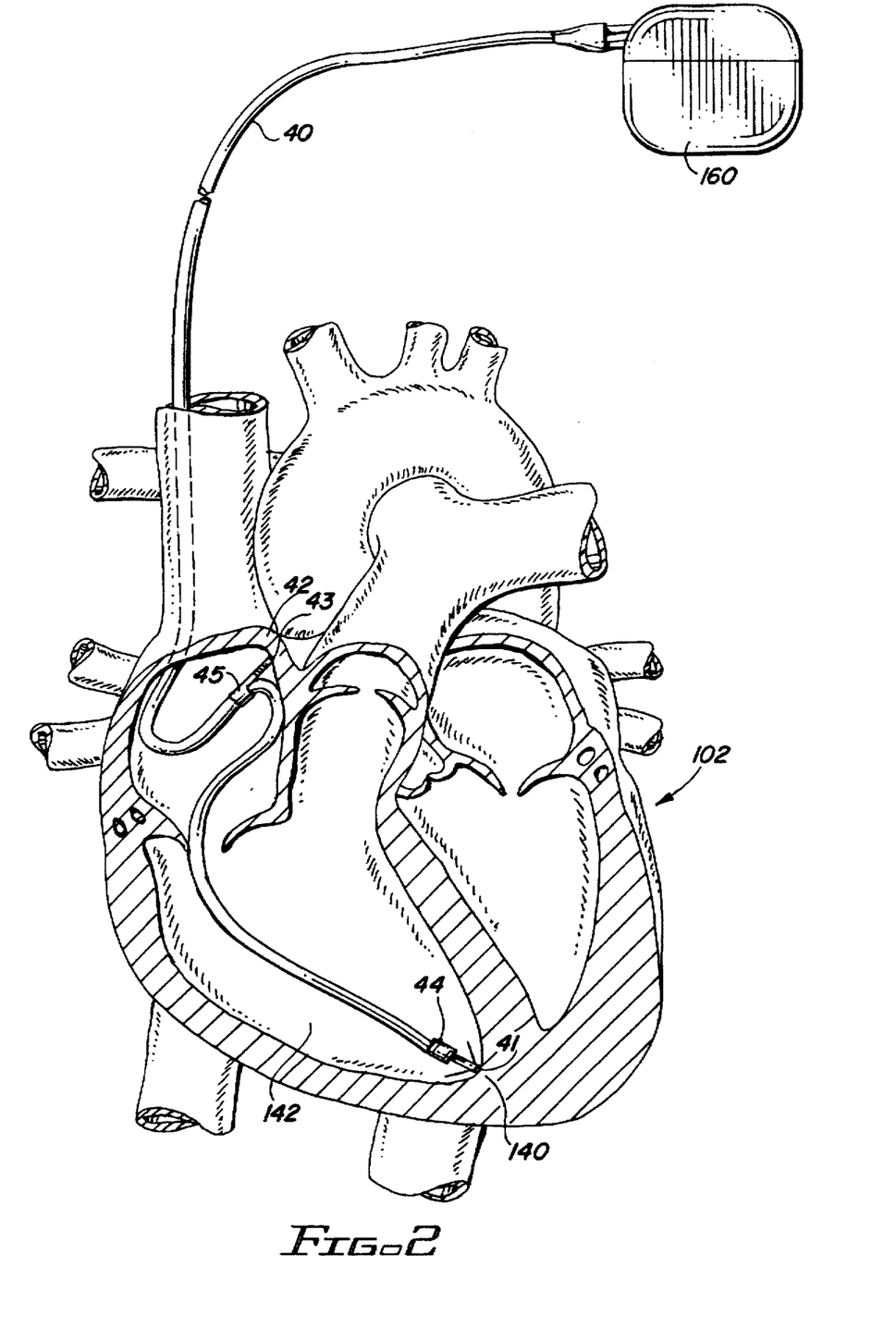
FIG. 2 is an isometric view of a heart having the pacemaker system of FIG. 1 implanted therein.

FIG. 2 illustrates the heart 102 with a single-pass pacing lead 40 with a ventricular electrode ventricular electrode tip 41 positioned within the right ventricle 142 of the heart 102. Further, in this embodiment, a pacing lead 40 has an electrode tip 43 which is positioned within the right atrium 152 of the heart 102. (While a single-pass lead 40 is shown in FIG. 2, this is for illustration purposes only, and one of ordinary skill in the art could easily replace this lead for two leads, either unipolar or bipolar, and not depart from the spirit of the invention. For the present invention, at least one lead is required located in the ventricle.)

The pacing lead 40 is preferably coupled to a case electrode 160 that is positioned within the body of the patient, such as under the pectoral muscle in a pectoral implant device. The processor 104 and the other related circuitry is positioned within the case electrode 160. As is understood in the art, the ventricular electrode ventricular electrode tip 41 acts as the sensor 106 and provides signals to the processor 104 via the sensing circuit 110 that are indicative of the functions of the heart. In particular, in the preferred embodiment, the sensor 106 provides signals to the processor which comprise an intracardiac electrogram.

Hence, the processor 104 receives signals which are indicative of the depolarization of the cardiac cells of the heart. Based upon these signals, the processor 104 can determine whether therapeutic shocks need to be applied to the heart to regulate heart function. Further, in the embodiment shown in FIGS. 1 and 2, both the right ventricle electrodes 41, 44 and the right atrial electrodes 43, 45 can be used to provide the unipolar or bipolar sense information to the sensor circuit indicative of the functioning of the heart (e.g., cardiac electrical signals). The operation of the pacing system 100 is, in this respect, similar to the operation of pacemakers of the prior art.

Figure 3:
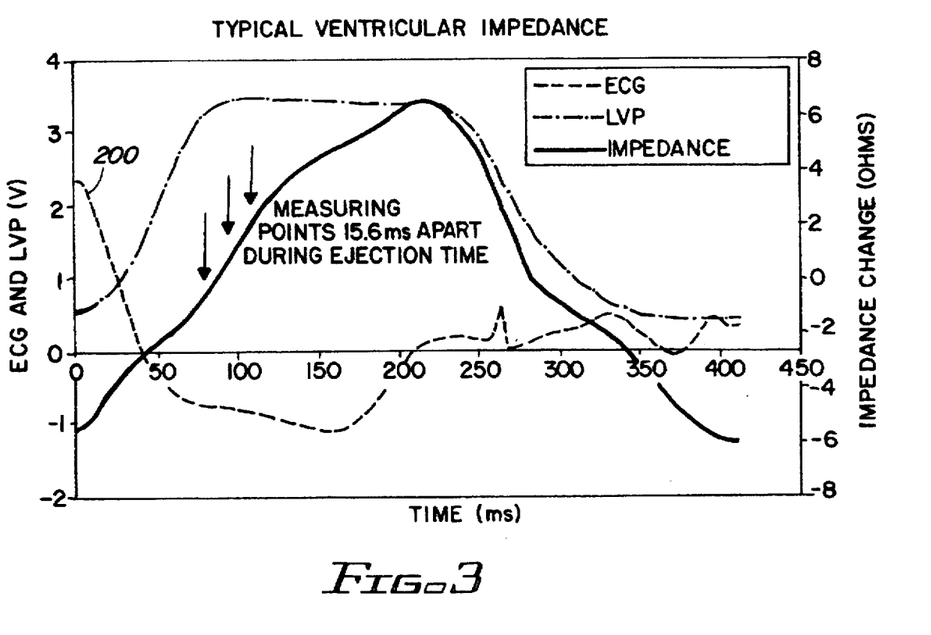
FIG. 3 is a diagram of a typical ventricular impedance waveform illustrating when impedance measurement signals are obtained by the system of FIG. 1.

However, the pacing system 100, which includes the impedance sensing circuit 125, obtains an impedance slope which is indicative of the contractility of the heart in the following manner. Specifically, in the preferred embodiment, the processor 104 receives a signal from the sensor circuit 110 which is indicative of the occurrence of a R-wave or a pacing pulse applied to the heart 102. As illustrated in FIG. 3, once the R-wave or pacing pulse has been detected, indicating the depolarization of the right ventricle 142 is occurring, the processor 104 then waits until a measurement window occurs during ventricular ejection, i.e., contraction of the right ventricle of the heart. More particularly, the measurement window occurs during late rapid ventricular ejection and early reduced ejection. During this window of time, the processor 104 triggers the timing and control circuitry 112 and the pulse generator 114 to provide a current pulse, preferably, to the ventricular electrode ring 44, or (if a unipolar lead is used) the ventricular electrode ventricular electrode tip 41. The impedance sensing circuit 125 then measures the voltage drop between two electrodes, for example, the ventricular electrode ventricular electrode tip 41 and the case electrode 160. The measurement of this voltage drop by the impedance sensing circuit 125 provides a first signal that is indicative of a first instantaneous impedance of the right ventricle of the heart during ventricular ejection. In the preferred embodiment, two or three such instantaneous measurements are taken during ventricular ejection at a 64 Hz sampling rate or approximately 15 milliseconds apart.

The instantaneous impedance values obtained at the 64 Hz sampling rate during ventricular ejection can then be used to calculate the slope dz/dt of the impedance during ventricular ejection by simply determining a difference between the measured impedance values. (Since the measurements are made over a predetermined time interval, there is no need to determine the actual slope which can be found by dividing this difference by the elapsed time during the measurement window.) As is shown in FIG. 3, the measurements are preferably taken at an interval of time that occurs approximately 50–200 milliseconds following the activity of the heart corresponding to the R wave 200 shown in FIG. 4. Most preferably, the measurements are taken during a 31 millisecond window centered at approximately 100 milliseconds following the occurrence of the activity of the heart corresponding to the R wave 200 as this point occurs during ventricular ejection.

Figure 4:
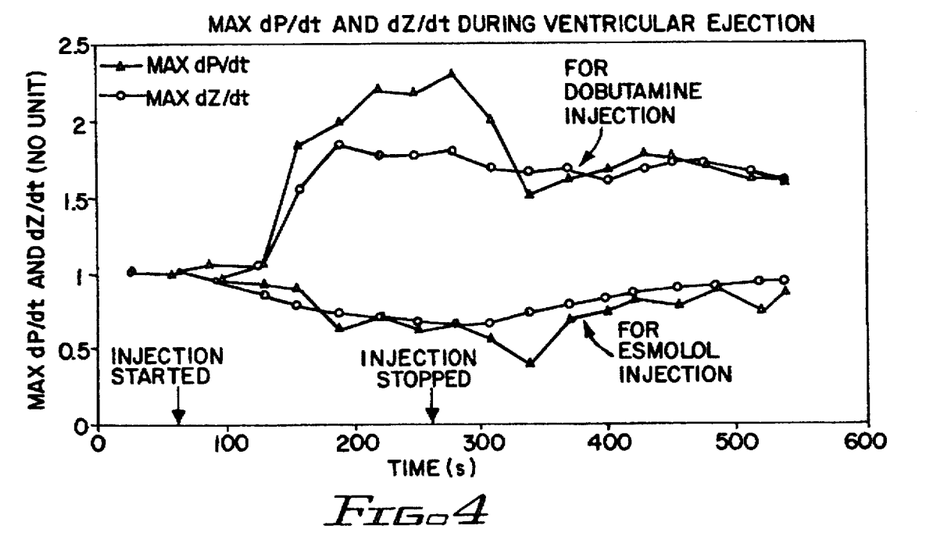
FIG. 4 is a diagram which illustrates the correlation between the maximum slope change in pressure during ventricular ejection and the slope change in impedance dz/dt during hemodynamic intervention.

More specifically, as shown in FIG. 3, the preferred measurement window occurs about the time that the pressure within the ventricle is reaching a maximum. For a typical patient, this occurs approximately 100 milliseconds following the cardiac activity corresponding to the R-wave or the paced beat. As is shown in FIGS. 3 and 4, and as will be discussed in greater detail below, the dz/dt is strongly correlated to the maximum slope of the ventricular pressure during ventricular ejection.

In the preferred embodiment, the impedance measurements are taken between the ventricular electrode ventricular electrode tip 41 and the case electrode 160 of the pacing lead 40. However, the impedance measurements can be determined by applying a current and measuring the voltage between at least any two electrodes including, for example, between the ventricular electrode ventricular electrode tip 41 and the ring electrode 44 provided that the current is applied via the ventricular ring electrode 44 positioned within the right ventricle of the heart.

Applicant has determined that the dz/dt as determined in the above-described manner strongly correlates to the maximum slope of the change in pressure within the ventricle (max dp/dt). In particular, FIG. 4 illustrates the correlation between the dz/dt measured and calculated in accordance with the principles described above with the change in the max dp/dt for five canines wherein the hemodynamics of the five canines were altered such that the cardiac contractility was modulated by both esmolol and dobutamine administration. As indicated in FIG. 4, the dz/dt closely tracks the max dp/dt for both dobutamine injection and for esmolol injection. As is understood, dobutamine administration increases the contractility of the heart, as is indicated by the increase in the max dp/dt measurements, and esmolol decreases the contractility of the heart as is indicated by the decrease in the max dp/dt measurements shown in FIG. 4. FIG. 4 also illustrates that the dz/dt tracks, and strongly correlates to, the measured max dp/dt contractility parameters. Consequently, the dz/dt, as determined by measuring the impedance during ventricular ejection at a 64 Hz sampling rate, provides a signal that strongly correlates with the contractility of the heart.

Figure 5A:
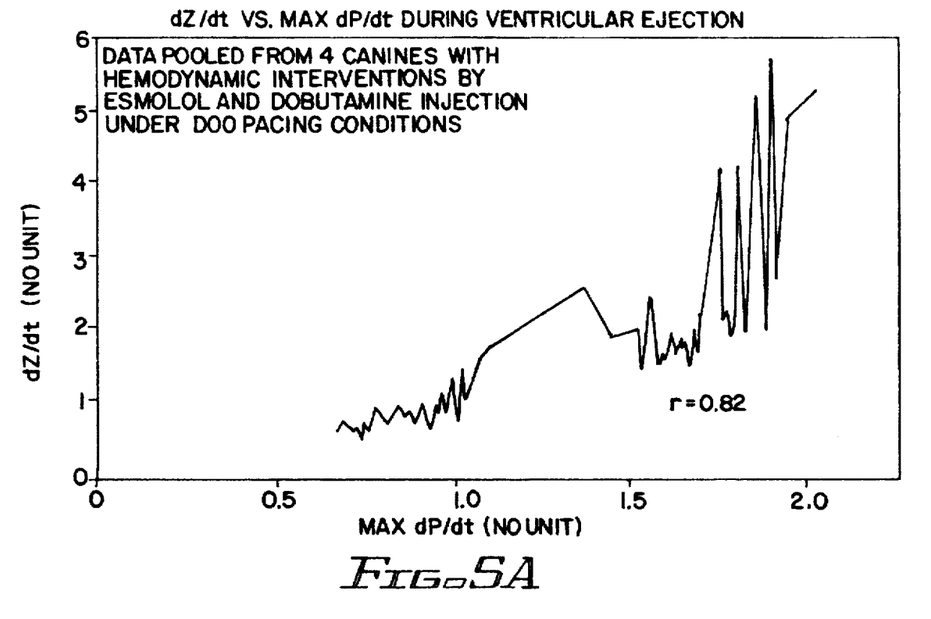
FIGS. 5A and 5B are diagrams illustrating the correlation between dz/dt versus maximum dp/dt during ventricular ejection for five canines with hemodynamic intervention.
Figure 5B:
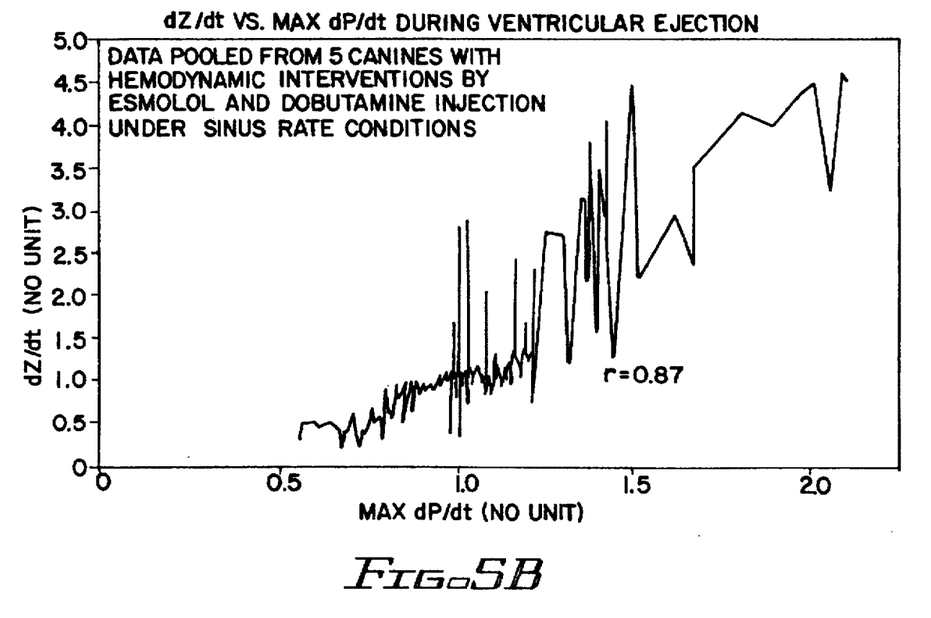

FIGS. 5A and 5B further illustrate this point. In FIG. 5A, data from four canines with hemodynamic interventions by esmolol and debutamine injection under DOO pacing conditions is plotted and the correlation between the dz/dt and max dp/dt is 0.82 for these four canines. Similarly, in FIG. 5B data from five canines with hemodynamic interventions by esmolol and debutamine injections under sinus rate conditions is plotted. There is a 0.87 correlation between the measured dz/dt as determined in accordance with the principles described above and a measured max dp/dt. Hence, Applicant believes that there is a very strong biological correlation between a slope of the impedance determined from two measured impedance values during ventricular ejection and the contractility of the heart.

Figure 6:
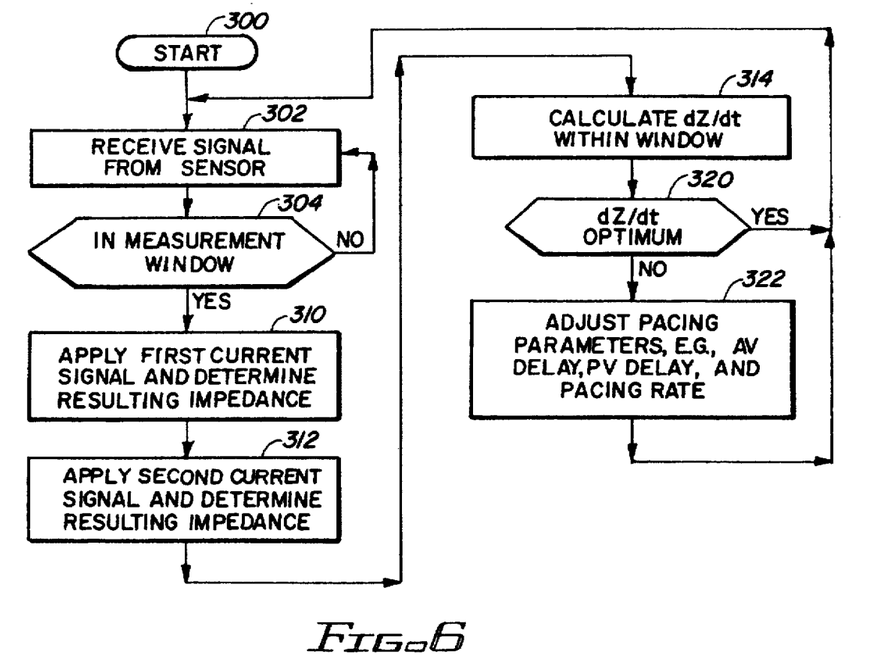
FIG. 6 is an exemplary flow chart illustrating the operation of the system of FIG. 1.

Hence, the pacemaker 100 of the preferred embodiment which senses the dz/dt in the above-described fashion can be used as a for controlling the operation of the processor 104 to optimize the performance of the pacemaker 100 and also to optimize the cardiac performance of the heart 102. FIG. 6 is an exemplary flow chart which illustrates an example of a process whereby the processor 104 can obtain the impedance dz/dt and then use this parameter to control the function of the pacing system 100 to optimize the performance of the pacing system and the heart. In particular, from a start state 300, the processor 104 receives from the sensor 106, via the sensing circuit 110, a signal indicative of the electrical depolarization of the heart in state 302. The processor 104 then determines whether the preferred measurement window has occurred in decision state 304.

In the preferred embodiment, the measurement window occurs approximately 50–150 milliseconds following the sensing of heart activity corresponding to the R wave 200 shown in FIG. 3. The window is more preferably a 15–100 millisecond window that is centered at a point which approximately corresponds to the point of maximum contraction of the heart, i.e., at a point during late rapid ventricular ejection and early reduced ejection. If the processor 104 determines that the R wave has not occurred, the processor 104 in this routine then continues to wait until the measurement window occurs.

Once the measurement window has occurred, the processor 104 in state 310 triggers the timing and control circuit 112 and the pulse generator 114 to generate an electrical impulse, specifically a current signal, that will emanate from the ventricular ring electrode 44 of the lead 40 that is positioned within the ventricle of the heart 102. The processor 104 then receives a signal from the impedance sensing circuit 125 indicative of the impedance between the ventricular electrode tip 41 and the case electrode 160 that occurs as a result of application of the current by the pulse generator 114 to the ventricular ring electrode 44.

The processor 104 then applies a second current pulse in state 312 approximately 15 milliseconds following the first current pulse and obtains the resulting impedance at this point in response to the signal received from the impedance sensing circuit 125. It will be understood that a third current signal can then be applied in the same manner as described above in reference to states 310 and 312 at the 64 Hz sampling rate so that three separate impedance values can be used to determine the impedance slope dz/dt within the measurement window in state 314.

The processor 104 can then determine in decision state 320 whether the dz/dt is indicative of an optimum performance of the pacemaker 100 for the patient given the characteristics of the patient and the sensed condition. It will be appreciated that the optimum performance can vary widely depending upon the patient, the observed conditions, and other factors. However, as an example, if the dz/dt can be maximized, generally the contractility of the heart can also be maximized. This means for a given heart rate, the amount of blood pumped for the heart can, therefore, also be maximized.

In the event that the processor 104 determines that the dz/dt is not indicative of optimum function of the heart, the processor 104 then uses information to adjust the pacing parameters to optimize heart performance in state 322. In particular, the processor 100 can alter the AV delay, increase the pacing rate, or otherwise alter the pacing signal and frequency of pacing to optimize the performance of the heart for the particular patient. Optimization of heart performance through pacing is discussed in co-pending patent application Ser. No. 08/736,891, filed Oct. 25, 1996, entitled "SYSTEM AND METHOD FOR PROVIDING HEMODYNAMICALLY OPTIMAL PACING", which is hereby incorporated by reference in its entirety. It will also be appreciated that the dz/dt can also be used to determine whether a pacing pulse has captured the heart, i.e., has induced a contraction of the ventricle. Specifically, if there was no capture, the dz/dt, as calculated above, would be below a predetermined threshold value.

It will be appreciated from the foregoing description that the pacing system 100 is capable of determining a slope of the impedance within the ventricle during ventricular ejection using a very small amount of power from the pacemaker's battery by taking discrete impedance measurements within the ventricle at discrete intervals during a window defined by the ventricular ejection of the heart. This parameter is, however, very indicative of the contractility of the heart and can, therefore, be used by a processor 104 of the pacing system 100 to change the function of the pacing system to improve or optimize the performance of the heart.

Although the foregoing description of the preferred embodiment of the present invention has shown, described and pointed out the fundamental novel features of the invention, it will be understood that various omissions, substitutions and changes in the form of the detail of the apparatus as illustrated as well as the uses thereof, may be made by those skilled in the art without departing from the spirit of the present invention. Consequently, the scope of the invention should not be limited to the foregoing discussion, but should be defined by the appended claims.

What is claimed is:

1. An implantable electrical system for delivering therapeutic shocks to a heart of a patient, the system comprising:
   a lead, which extends into a ventricle of the heart, adapted for delivering electrical pulses;
   control means for selectively inducing the lead to deliver an impedance measurement excitation pulse and pacing pulses to the ventricle to regulate the function of the heart;
   measuring means, in response to the delivered excitation pulse, for measuring at least two instantaneous impedance measurements in the heart, wherein the impedance measurement excitation pulses are delivered to the heart at at least two different times during a measurement window to determine a single slope, the window being selected to coincide with contraction of the ventricle;
   means for determining an impedance slope based on the instantaneous impedance measurements, the impedance slope being indicative of contractility of the heart; and
   means for regulating the heart function based on the impedance slope.

2. The system of claim 1, wherein the means for determining the impedance slope comprises:
   means for determining the difference between the instantaneous impedance measurements at the at least two different times.

3. The system of claim 2, wherein the control means comprises:
   means for inducing the lead to deliver the impedance measurement excitation pulse at approximately a 64 Hz sampling rate during the measurement window.

4. The system of claim 1, further comprising:
   sensing means for sensing a ventricular contraction;
   timing means for triggering the measurement window to occur approximately 50-150 milliseconds after a ventricular contraction, and for triggering a sampling interval for the at least two instantaneous impedance measurements to be at least 15 ms apart.

5. The system of claim 1, wherein the control means comprises:
   means for adjusting the pacing pulses to optimize the pumping function of the heart based on the impedance slope.

6. The system of claim 5, wherein the adjusting means comprises:
   means for adjusting at least one of AV delay or PV delay until the measured impedance slope is maximized.

7. The system of claim 5, wherein the adjusting means comprises:
   means for adjusting at least pacing rate until the measured impedance slope is maximized.

8. The system of claim 7, further comprising:
   sensing means for sensing cardiac signals and for providing the control means with a signal that is indicative of contractions of the heart;
   wherein the control means includes means for defining the measurement window as a window of time synchronous with the contraction of the heart corresponding to a period of late rapid ventricular ejection and early reduced ventricular ejection.

9. The system of claim 8, wherein the control means comprises:

means for inducing the lead to deliver the at least two impedance measurement excitation pulses during the measurement window at an interval of approximately 15 milliseconds.

10. The system of claim 1, wherein:

the lead includes a ventricular tip and a ring electrode coupled to the control means so that the impedance measurement excitation pulse emanates from the ventricular ring electrode; and the impedance measurement means includes means for measuring the impedance between the ventricular electrode tip and a case electrode.

11. A pacing system for delivering pacing pulses to a heart comprising:

one or more leads positioned within one or more chambers of the heart including the right ventricle; and control means for selectively inducing the one or more leads to provide electrical pulses to the respective chamber of the heart, and for measuring an instantaneous impedance within the heart, wherein the control means induces the leads to provide a first type of electrical pulse for pacing purposes, and wherein the control means induces the leads to provide a second type of electrical pulse defined by a window which occurs during a contraction of the ventricle of the heart so that the instantaneous impedance within the heart can be measured by the control means at at least two instances within the window, wherein the control means uses the two measured instantaneous impedance values to determine an impedance slope that corresponds to the contractility of the ventricle of the heart, and wherein the control means includes means for altering the delivery of the first electrical pulse to the heart based on the impedance slope.

12. The system of claim 11, wherein:

the at least one lead includes a lead that is positioned within the right ventricle of the heart; and the second electrical pulses are provided to the right ventricle of the heart so that the control means can obtain an impedance slope during contraction of the right ventricle that has a high correlation to the contractility of the right ventricle during ventricular ejection.

13. The system of claim 12, wherein:

the one or more leads also includes a lead that is positioned within the right ventricle of the heart; and the control means uses the impedance slope to adjust at least one of an AV delay, a PV delay, or pacing rate during pacing to increase the volume of blood pumped by the heart during ventricular ejection.

14. The system of claim 12, wherein the control means comprises:

means for inducing the at least one lead to deliver the second type of electrical pulse to the heart during the window so that at least two separate impedance measurements are made during the window at least 15 milliseconds apart.

15. The system of claim 11, wherein the difference between the instantaneous impedance measurements at the at least two different times corresponds to the impedance slope.

16. The system of claim 15, wherein the control means comprises:

means for adjusting the pacing pulses based on the impedance slope to optimize the pumping function of the heart.

17. The system of claim 16, further comprising:

sensing means for sensing cardiac signals of the heart and for providing the control means with a signal that is indicative of contractions of the heart.

18. The system of claim 17, wherein the control means comprises:

means for defining the measurement window as a window of time occurring approximately 50–150 milliseconds after the sensing means provides a signal indicative of a contraction.

19. The system of claim 18, wherein:

the at least one lead includes a ventricular tip and ring electrode;

the impedance measurement excitation pulse emanates from the ventricular ring electrode; and the impedance measurement means measures the instantaneous impedance between the ventricular electrode tip and a case electrode.

20. The system of claim 11, wherein the control means is comprised of:

sensing means for receiving signals from the one or more leads that are indicative of the function of the heart;

pulse generator means for generating the first and second electrical pulses to the heart;

impedance measurement means for measuring the instantaneous impedance in the ventricle of the heart in response to the pulse generator means generating the second type of electrical pulse; and processing means, in response to signals from the sensing means and the impedance measurement means, for providing signals to the pulse generator means to provide the first and second type of electrical pulses to the heart.

21. An implantable system for providing therapeutic electrical pulses to the heart of a patient comprising:

delivery means for delivering electrical pulses to a ventricle of the heart;

control means for controlling the delivery of the electrical pulses to the ventricle of the heart, wherein the control means induces the delivery means to provide a first type of electrical pulse for therapeutic purposes and a second type of electrical pulse for impedance measurement purposes; and means for adjusting the first electrical pulses to optimize hemodynamics by measuring at least two instantaneous impedance measurements during a window defined by contraction of the ventricle of the heart to determine a single impedance slope representative of the instantaneous impedance slope that corresponds to the contractility of the ventricle of the heart.

22. The system of claim 21, wherein the delivery means comprises:

at least one lead having a tip electrode that is positioned adjacent the inner wall of the right ventricle of the heart; and a return electrode for electrical pulses provided to the heart.

23. The system of claim 22, wherein the control means comprises:

means for obtaining a measurement of the instantaneous impedance during ventricular ejection based on the impedance measured between the tip and the case electrode whenever the second electrical pulse is produced between the ring and case electrode.

24. The system of claim 23, further comprising:

sensing means for sensing contractions of the heart and for providing a signal to the control means; and wherein the control means includes means for inducing the delivery means to deliver the second type of electrical pulses to the heart after sensing a ventricular contraction so that the second electrical pulses are provided during a period of ventricular ejection.

25. The system of claim 24, wherein the control means comprises:

means for inducing the delivery means to deliver the second type of electrical pulses at a rate of about 64 Hz during a window that is approximately 50–150 milliseconds following the sensing of either a naturally occurring contraction or an evoke contraction.

26. The system of claim 25, wherein the control means comprises:

means for determining the difference between the instantaneous impedance measurements corresponding to the impedance slope.

27. The system of claim 26, wherein the control means comprises:

means for adjusting the delivery of the first type of electrical pulse to the heart to increase the impedance slope.

28. A method of providing electrical pulses to the heart of a patient comprising the steps of:

sensing the occurrence of either an evoke contraction or a naturally occurring contraction;

providing two impedance measurement pulses to a ventricle of the heart during either the evoked contraction or the naturally occurring contraction;

obtaining two instantaneous impedance measurements in response to the two impedance measurement pulses;

determining an impedance slope based on the two instantaneous impedance measurements; and adjusting the delivery of one or more pacing electrical pulses to the heart based upon the determined impedance slope.

29. The method of claim 28, wherein the step of providing two impedance measurement pulses to a ventricle comprises the step of:

providing two impedance measurement pulses to the right ventricle via a pacing lead having a tip and a ring electrode that is positioned within the right ventricle.

30. The method of claim 29, wherein the step of obtaining two impedance measurements during the window of time comprises the step of:

measuring the instantaneous impedance between a selected return electrode and the tip electrode.

31. The method of claim 30, wherein the step of determining an impedance slope comprises the step of:

determining the difference between the instantaneous impedance measurements at at least two different times.

32. The method of claim 31, wherein the step of providing the two impedance measurement pulses comprises the step of:

providing the two impedance measurement pulses at a rate of about 64 Hertz during a window of time occurring approximately 50–150 milliseconds following the sensing of either the evoke contraction or the naturally occurring contraction.

33. The method of claim 32, wherein the step of adjusting the delivery of one or more pacing electrical pulses to the heart based upon the determined impedance slope comprises the step of:

adjusting at least one of the pacing rate, the AV delay or the PV delay to increase the impedance slope for subsequent measurements.

34. An implantable electrical system for delivering therapeutic stimulation to a patient's heart, the system comprising:

a lead, which extends into a ventricle of the heart, adapted for delivering electrical pulses;

a pulse generator, coupled to the lead, that selectively generates one of tissue stimulation pulses or impedance excitation pulses to the ventricle, wherein the impedance excitation pulses are delivered at two different times during a period of ventricular ejection corresponding to contraction of the ventricle;

an impedance measuring circuit, coupled to the lead, that measures an instantaneous impedance at the two different times the excitation pulses are delivered during the ventricular contraction;

a processor system, coupled to the impedance sensing circuit and the pulse generator, that determines an impedance slope based on the two instantaneous impedance measurements, the impedance slope being indicative of contractility of the ventricle, and that regulates the generation of the tissue stimulation pulses based on the impedance slope.

* * * * *